United States Patent
Tischenko et al.

(10) Patent No.: US 8,971,481 B2
(45) Date of Patent: Mar. 3, 2015

(54) TOMOGRAPHY APPARATUS AND TOMOGRAPHY METHOD

(75) Inventors: Oleg Tischenko, München (DE); Hugo De Las Heras, München (DE); Christoph Hoeschen, Hebertshausen (DE)

(73) Assignee: Helmholtz Zentrum Munchen Deutsches Forschungszentrum für Gesundheit und Umwelt (GmbH) (DE)

( * ) Notice: Subject to any disclaimer, the term of this patent is extended or adjusted under 35 U.S.C. 154(b) by 641 days.

(21) Appl. No.: 13/320,175

(22) PCT Filed: May 10, 2010

(86) PCT No.: PCT/EP2010/002862
§ 371 (c)(1),
(2), (4) Date: Jan. 23, 2012

(87) PCT Pub. No.: WO2010/130394
PCT Pub. Date: Nov. 18, 2010

(65) Prior Publication Data
US 2013/0039459 A1    Feb. 14, 2013

(30) Foreign Application Priority Data
May 13, 2009   (EP) .................................. 09006483

(51) Int. Cl.
*A61B 6/03*    (2006.01)
*G21K 1/02*    (2006.01)
*A61B 6/06*    (2006.01)
*A61B 6/00*    (2006.01)

(52) U.S. Cl.
CPC ................ *G21K 1/025* (2013.01); *A61B 6/032* (2013.01); *A61B 6/06* (2013.01); *A61B 6/542* (2013.01); *A61B 6/4028* (2013.01)
USPC .................................................. 378/16; 378/4

(58) Field of Classification Search
CPC ................................ A61B 6/032; A61B 6/027
USPC ......................................... 378/10, 122, 4, 16
See application file for complete search history.

(56) References Cited

U.S. PATENT DOCUMENTS 4,315,157 A *   2/1982   Barnes ........................... 378/10
7,885,375 B2 *  2/2011   Bernard De Man et al. ..... 378/9

FOREIGN PATENT DOCUMENTS

| EP | 1 677 253 A1 | 7/2006 |
| EP | 1 780 676 A1 | 5/2007 |
| WO | WO2007/004859 A1 * | 3/2007 |
| WO | 2007/048590 A1 | 5/2007 |

* cited by examiner

*Primary Examiner* — Hoon Song
(74) *Attorney, Agent, or Firm* — DLA Piper LLP (US)

(57) ABSTRACT

A tomography apparatus that generates images of an object includes a radiation source emitting a radiation beam, wherein the radiation beam rotates around the object and penetrates the object; a radiation detector rotating around the object opposite the radiation source so that the radiation detector detects the radiation beam after penetration of the object; a radiation mask surrounding the object that masks the radiation beam, wherein the radiation mask is arranged in a path of the radiation beam between the radiation source and the radiation detector and the radiation beam passes the radiation mask only once between the radiation source and the radiation detector.

10 Claims, 6 Drawing Sheets

TOMOGRAPHY APPARATUS AND TOMOGRAPHY METHOD

RELATED APPLICATIONS

This is a §371 of International Application No. PCT/EP2010/002862, with an international filing date of May 10, 2010 (WO 2010/130394 A1, published Nov. 18, 2010), which is based on European Patent Application No. 09006483.3, filed May 13, 2009, the subject matter of which is incorporated by reference.

TECHNICAL FIELD

This disclosure relates to a tomography apparatus and a tomography method for generating images of an object, e.g., a patient.

BACKGROUND

Conventional computer tomography apparatuses of the third generation are disclosed, for example, in WO 2007/048590 A1. One problem associated with these conventional computer tomography apparatuses is that high doses of radiation are applied to the patient during scanning Further, U.S. Pat. No. 4,315,157 discloses a computer tomograph comprising a stationary radiation detector. Therefore, this patent follows a different approach.

Moreover, reference is made to EP 1 780 676 A1 and EP 1 677 253 A1.

Therefore, it could be helpful to reduce the radiation doses which are applied during a scanning process. Particularly, it could be helpful to provide a tomography apparatus and a tomography method which is applying a reduced radiation dose to the patient during scanning

SUMMARY

We provide a tomography apparatus that generates images of an object, including a) a radiation source emitting a radiation beam, wherein the radiation beam rotates around the object and penetrates the object, b) a radiation detector rotating around the object opposite the radiation source so that the radiation detector detects the radiation beam after penetration of the object, c) a radiation mask surrounding the object that masks the radiation beam, wherein the radiation mask is arranged in a path of the radiation beam between the radiation source and the radiation detector, and d) the radiation beam passes the radiation mask only once between the radiation source and the radiation detector.

We also provide a tomography method that generates sectional images of an object in a measurement plane, including a) emitting a radiation beam by a radiation source, wherein the radiation beam rotates in the measurement plane relative to the object and penetrates the object, b) detecting the radiation beam with a radiation detector after penetration of the object, and c) masking the radiation beam by a radiation mask which surrounds the object and is arranged in a path of the radiation beam between the radiation source and the radiation detector, wherein d) the radiation beam passes the radiation mask only once between the radiation source and the radiation detector.

LIST OF REFERENCE NUMERALS

1 Computer tomography apparatus
2 Radiation source
3 Radiation detector
5 Object
6 Circular path
7 Radiation beam
8 Radiation mask
7A, 7B Sectors of radiation mask
8 Mask plane
9 Measurement plane
10 Center axis
11 Surface normal of radiation mask
12 Electron beam
13 Target point

DETAILED DESCRIPTION

We provide novel tomography apparatus that generates images of an object (e.g., a patient) comprising a radiation source (e.g., an X-ray source) emitting a radiation beam, wherein the radiation beam rotates around the object and penetrates the object.

It is preferred that the tomography apparatus generates sectional two-dimensional images of the object in a specific measurement plane. In such a case, the radiation beam can be restricted to the measurement plane. For example, the radiation beam can be fan-shaped and aligned coplanar with the measurement plane.

However, it is alternatively possible that the tomography apparatus generates three-dimensional images. In such a case, the radiation beam extends axially with regard to the rotary axis of the radiation beam so that the radiation beam penetrates the object not only in a single measurement plane, but over the entire length or at least a portion of the object. This can be advantageous since the entire volume of the object can be scanned during a single rotation of the radiation beam.

Further, the novel tomography apparatus comprises a radiation detector rotating around the object opposite the radiation source so that the radiation detector detects the radiation beam after penetration of the object. It has already been mentioned that we follow a different approach than the afore-mentioned U.S. Pat. No. 4,315,157 in which the radiation detector is arranged stationary. All aspects of the apparatus are therefore linked by the special technical feature defining that the radiation detector rotates around the object.

Moreover, the novel tomography apparatus comprises a radiation mask for masking the radiation beam, wherein the radiation mask is arranged in the path of the radiation beam between the radiation source and the radiation detector.

The novel tomography apparatus is characterized in that the radiation beam passes the radiation mask only once between the radiation source and the radiation detector so that the radiation dose applied during scanning can be reduced.

The radiation mask may be ring-shaped and surrounds the object in a first example. Such a configuration is disclosed, for example, in the afore-mentioned WO 2007/048590 A1 which is hereby incorporated herein by reference. In this case, the radiation detector is arranged inside the ring-shaped radiation mask so that the radiation beam passes the radiation mask only once on its path from the radiation source to the radiation detector, thereby allowing a reduction of the radiation doses applied during scanning The radiation mask may also be ring-shaped and surrounds the object in a second example. However, this structure provides that the radiation detector is arranged outside the ring-shaped radiation mask as disclosed, for example, in the afore-mentioned WO 2007/048590 A1. Therefore, the mask plane (i.e., the midplane or center plane of the mask) is tilted relative to the measurement plane, wherein the mask plane intersects the measurement plane so that the radiation beam passes the radiation mask only once on its path between the radiation source and the radiation detector. In other words, the ring-shaped radiation mask is tilted relative to the measurement plane such that one side of the radiation mask is in the measurement plane and therefore affects the radiation beam while the opposing side of the radiation mask is tilted out of the measurement plane and therefore does not affect the radiation beam.

In the afore-mentioned structure, the radiation mask preferably performs a precession movement around an axis perpendicular to the measurement plane so that a surface normal of the mask plane is always facing the radiation source. In other words, a fixed angular position of the radiation mask relative to the radiation beam is maintained while the radiation beam is rotating around the object (e.g., a patient) during scanning Therefore, the afore-mentioned precession movement of the radiation mask is preferably synchronized with the rotation of the radiation beam. It should further be mentioned that the mask plane and the measurement plane include a predetermined tilt angle, wherein the tilt angle can be greater than 2°, 5°, 7° or 10° and/or smaller than 60°, 45°, 30° or even smaller than 25°. However, our apparatus is not restricted to the afore-mentioned exemplary values of the tilt angle.

The radiation mask may also be ring-shaped and arranged around the object in a third example, wherein the radiation detector is arranged outside the ring-shaped radiation mask. The radiation mask thus comprises several adjacent sectors which are distributed around the object along the circumference of the ring-shaped radiation mask. The individual sectors of the radiation mask can be moved selectively into the path of the radiation beam or out of the path of the radiation beam so that the radiation beam passes the radiation mask only once on its path between the radiation source and the radiation detector. On one side of the radiation mask, the sectors of the radiation mask are moved into the path of the radiation beam, while the sectors on the opposing side of the radiation mask are moved out of the radiation beam so that the radiation beam penetrates only one sector of the radiation mask, thereby allowing a reduction of the radiation doses applied during scanning The sectors of the radiation mask may therefore preferably be moveable orthogonally to the mask plane or parallel to the rotary axis of the radiation beam.

Further, the radiation mask preferably comprises N shielding elements which are separated by radiation windows wherein the shielding elements are arranged around the object. Further, the radiation mask preferably comprises n selectively moveable sectors each extending over an angle of 360°/n around the object. Moreover, there is preferably a specific relationship $$3 \leq n \leq N$$

between the number N of shielding elements and the number n of the moveable sectors of the radiation mask.

It has already been mentioned that we provide that the radiation mask surrounds the object. This preferably means that an axial view of the tomography apparatus shows that the radiation mask surrounds the object with regard to the rotational axis of the radiation beam and the radiation detector. However, it is not necessary that the entire radiation mask is arranged in a single plane and surrounds the object. It is rather sufficient if the axial projection of the radiation mask surrounds the object.

The radiation mask may be only partially ring-shaped and open on one side in a fourth example, thereby avoiding a second collimation of the radiation beam on its path to the radiation detector. The radiation mask thus covers a predetermined angle around the object, wherein the angle of coverage is preferably 180°-270°.

The radiation mask may therefore preferably be partially ring-shaped and surrounds the object. However, the sector-shaped opening in the radiation mask allows an arrangement of the radiation detector outside the ring-shaped radiation mask.

The radiation mask may also preferably be discretely moved around the object at predetermined angular steps a and the radiation mask preferably comprises N shielding elements which are separated by radiation windows, wherein the shielding elements are angularly arranged around the object. The angular steps a are preferably α=360°/N.

Further, we provide another apparatus as a fifth example wherein the radiation source comprises a ring-shaped anode surrounding the object, preferably in the measurement plane. Both the radiation source and the ring-shaped anode can thus be arranged fixedly. However, the radiation source comprises an electron source directing the electron beam onto the ring-shaped anode surrounding the object thereby generating the radiation beam as a secondary X-radiation beam. The ring-shaped anode therefore comprises several anode elements which are spaced apart and distributed around the object so that the anode constitutes the radiation mask. Further, the electron beam is moved around the ring-shaped anode along the circumference of the ring-shaped anode, so that the secondary X-radiation beam rotates around the object.

The radiation detector may preferably rotate around the object, wherein the electron beam and the radiation detector are moved in the same direction and with the same angular speed around the object so that the radiation detector and the target point of the electron beam on the ring-shaped anode are always on opposite sides of the object so that the secondary X-radiation beam penetrates the object on its path to the radiation detector. It should further be noted that the electron beam is preferably aligned substantially parallel or acute-angled to the surface normal of the measurement plane. In other words, the electron beam preferably rotates on the surface shell of a cone wherein the circumference of the ground area of the cone is constituted by the ring-shaped anode.

The radiation detector can be flat or curved in the measurement plane.

In the afore-mentioned first example of our apparatus, the radiation detector is arranged inside the ring-shaped radiation mask and preferably extends up to the size that is enough to cover the radiation after penetration of the object surrounded by the radiation mask.

Further, the radiation mask can be arranged fixedly, which is preferred in that example.

Moreover, the radiation beam is preferably fan-shaped and substantially co-planar with the measurement plane so that the fan-shaped radiation beam penetrates the entire section of the object in the measurement plane.

Alternatively, the radiation beam is cone-shaped and in this case the central fan of the cone beam is co-planar with the central plane of the ring.

It should further be noted that the radiation detector is preferably radiation-sensitive along a predetermined extension along the measurement plane and/or along the rotary axis of the radiation beam. This contrasts to a radiation detector comprising a point-shaped sensitivity.

Further, the radiation beam penetrating the object is preferably an X-radiation beam. However, it is theoretically possible to use other types of radiation so that our apparatus is not restricted to X-radiation.

It should further be noted that the radiation mask is preferably made of a material which is radiation absorbing, particularly lead or tungsten.

Moreover, the radiation source and the radiation detector are preferably arranged on a gantry on opposite sides of the object, wherein the gantry rotates in the measurement plane.

Further, the radiation beam, the radiation source and the radiation detector preferably carry out coaxial rotary motions.

It should further be noted that the radiation detector preferably rotates in the same direction and at the same angular speed around the object as the radiation beam. In the afore-mentioned fifth example, the radiation source can be arranged fixedly while the secondary radiation beam rotates around the object. However, in other examples, the radiation source itself rotates around the object.

Moreover, it should be noted that our apparatus preferably relates to a computer tomography apparatus of the third generation, i.e., a rotate/rotate device comprising both a rotating radiation source and a rotating radiation detector. However, our apparatus is not restricted to a tomography apparatus of the third generation.

Finally, it should be noted that our apparatus is not restricted to the afore-mentioned tomography apparatus but rather comprises a corresponding method, as well.

Our apparatus and methods and their particular features and advantages will become more apparent from the following detailed description considered with reference to the accompanying drawings.

Figure 1:
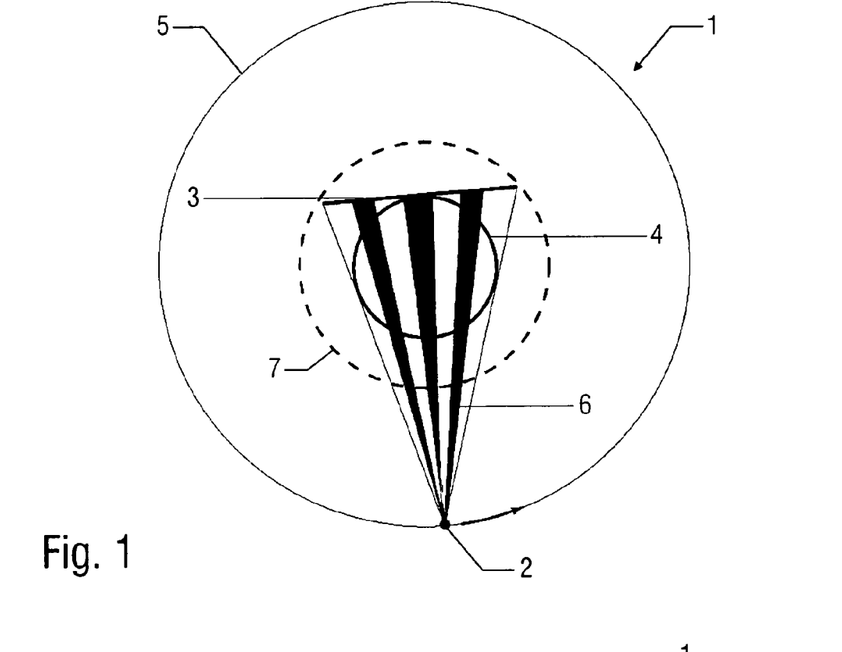
FIG. 1 is a sectional view of a tomography apparatus according to a first example, wherein the radiation detector is arranged inside the ring-shaped radiation mask.

FIG. 1 shows a sectional view of a computer tomography apparatus 1 of the so-called "third generation," i.e., the computer tomography apparatus 1 comprises a rotating radiation source 2 and a rotating radiation detector 3.

The computer tomography apparatus 1 can be used for generating sectional images of an object 4 (e.g., a patient) in a measurement plane which is identical with the cutting plane shown in the drawing.

The radiation source 2 rotates around the object 4 on a circular path 5 in the direction of the arrow, i.e., counter-clockwise.

Further, the radiation detector 3 rotates around the object 4 in the direction of the arrow counter-clockwise, wherein the rotation of the radiation source 2 and the rotation of the radiation detector 3 are synchronized so that the radiation source 2 and the radiation detector 3 are always on opposite sides of the object 4.

The radiation source 2 emits a fan-shaped radiation beam 6 which is coplanar with the measurement plane, wherein the fan angle of the radiation beam 6 is sufficiently large that the fan-shaped radiation beam 6 covers the entire lateral extension of the object 4 in the measurement plane.

Further, the computer tomography apparatus 1 comprises a ring-shaped radiation mask 7 surrounding the object 4, wherein the radiation mask 7 is arranged coaxially to the circular path 5 of the radiation source 2.

The radiation mask 7 consists of a large number of shielding elements arranged along the circumference of the ring-shaped radiation mask 7 so that the individual shielding elements of the radiation mask are separated by radiation windows which can be penetrated by the radiation beam 6. On the contrary, the shielding elements of the radiation mask 7 consist of a material with high radiation absorption properties like lead (Pb) or tungsten (W). Along the circumference of the radiation mask 7, the shielding elements alternate with radiation windows of the same size.

The novel computer tomography apparatus 1 differs from conventional computer tomography apparatuses in that the radiation source is outside of the ring-shaped mask and the radiation detector 3 is arranged inside the ring-shaped radiation mask 7 so that the radiation beam 6 passes the radiation mask 7 only once on its path between the radiation source 2 and the radiation detector 3. This is advantageous since it allows a significant reduction of the radiation doses applied during scanning of the object 4.

It should further be noted that the radiation detector 3 is flat and extends laterally up to the inside of the radiation mask 7.

Figure 2:
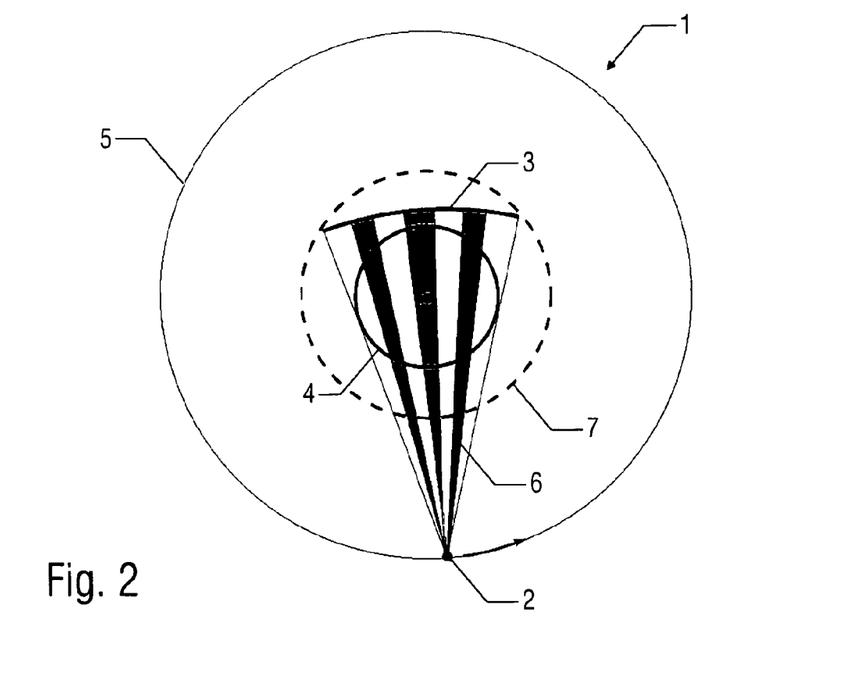
FIG. 2 is a modification of FIG. 1 including a curved radiation detector instead of a flat radiation detector.

FIG. 2 shows a modification of the first example as shown in FIG. 1 so that reference is made to the above description and the same reference numerals are used for corresponding parts and details.

One characteristic feature of this modification is that the radiation detector 3 is not flat but curved.

Figure 3A:
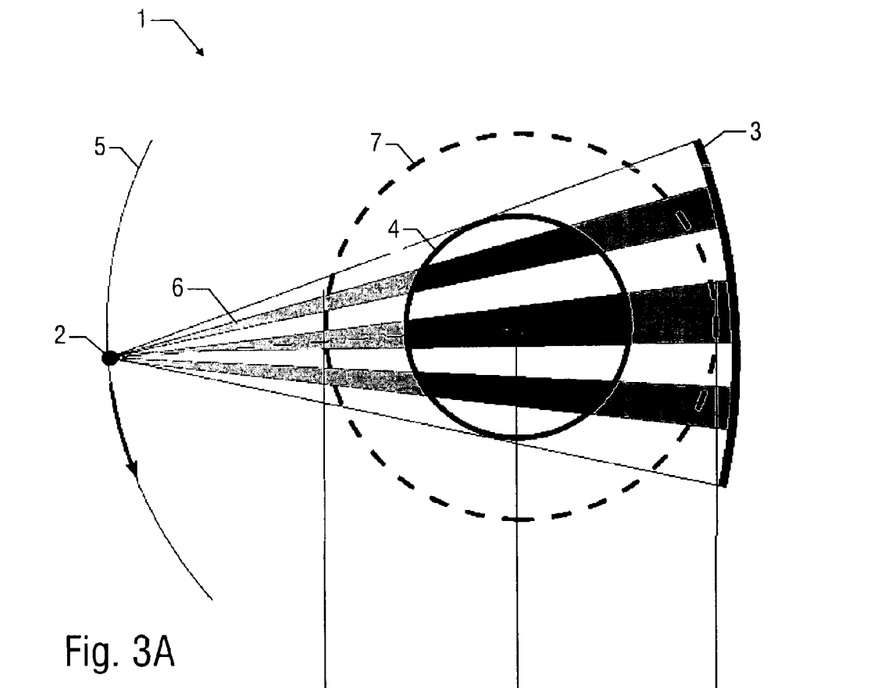
FIG. 3A is a sectional view of a second example, wherein the radiation detector is arranged outside the ring-shaped radiation mask and the radiation mask is tilted relative to the measurement plane.
Figure 3B:
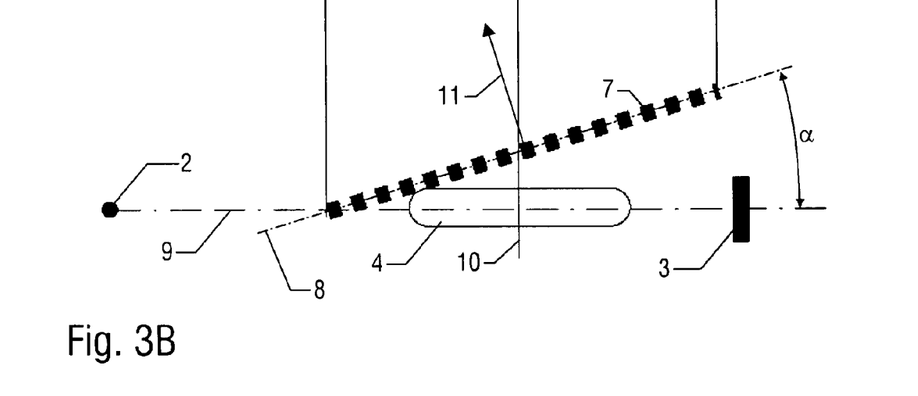
FIG. 3B is a side view of the second example according to FIG. 3A.

FIGS. 3A and 3B illustrate the afore-mentioned second example, which is similar to the afore-mentioned first example so that reference is made to the above description and the same reference numerals are used for corresponding parts and details.

First, it has to be noted that the radiation detector 3 is arranged outside the ring-shaped radiation mask 7.

Further, it has to be noted that the radiation mask 7 is arranged in a mask plane 8 which is tilted relative to the measurement plane 9 by a tilt angle $\alpha \approx 20°$ so that the radiation beam 6 passes the radiation mask 7 on one side only, i.e., between the radiation source 2 and the object 4, while the other side of the radiation mask 7 is tilted out of the measurement plane 9 and therefore does not affect the radiation beam 6.

It should further be noted that the radiation mask 7 carries out a precession movement around a center axis 10 so that a surface normal 11 of the radiation mask 7 always faces the radiation source 2.

Figure 4A:
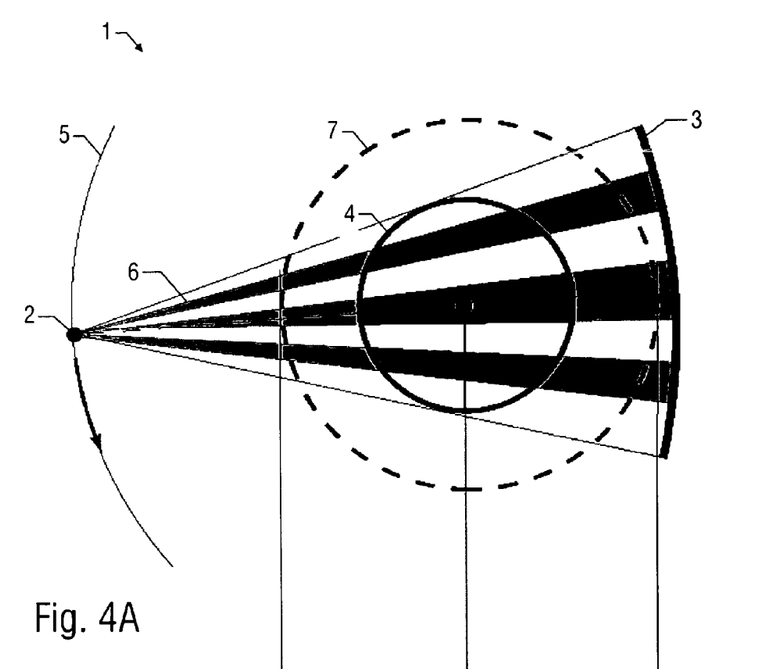
FIG. 4A is a sectional view of a third example in which the radiation mask includes several sectors which can be selectively moved into the path of the radiation beam or out of the path of the radiation beam.
Figure 4B:
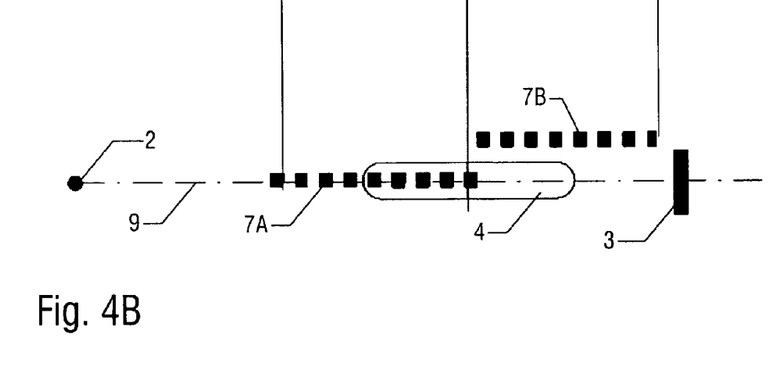
FIG. 4B is a side view of the example according to FIG. 4A.

FIGS. 4A and 4B illustrate the afore-mentioned third example which is similar to the other examples so that reference is made to the above description and the same reference numerals are used for corresponding parts and details.

The radiation mask 7 consists of several sectors 7A, 7B which can be moved selectively into the measurement plane 9 or out of the measurement plane 9. In FIG. 4B, the sector 7A is moved into the measurement plane 9 while the opposing sector 7B is moved out of the measurement plane 9. Therefore, the sector 7A of the radiation mask 7 affects the radiation beam 6 while the opposing sector 7B of the radiation mask 7 does not affect the radiation beam 6 since it is moved out of the measurement plane 9.

The movement of the sectors 7A, 7B of the radiation mask 7 is controlled such that the radiation beam 6 passes only one of the opposing sectors 7A, 7B of the radiation mask 7.

Figure 5A:
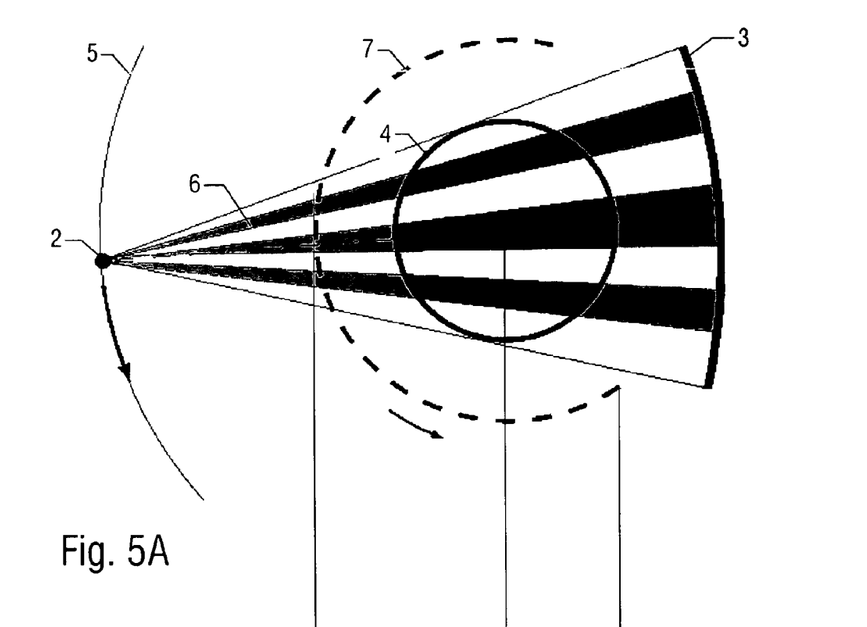
FIG. 5A is a sectional view of a fourth example in which a radiation mask is partially ring-shaped and open on one side so that the radiation detector can be arranged outside the radiation mask.
Figure 5B:
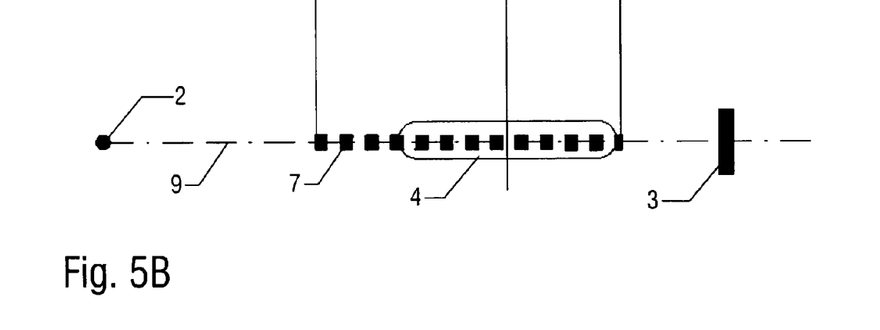
FIG. 5B is a side view of the example according to FIG. 5A.

FIGS. 5A and 5B illustrate the afore-mentioned fourth example which is partially similar to the other examples so that reference is made to the above description and the same reference numerals are used for corresponding parts and details.

The radiation mask 7 is partially ring-shaped but open on one side. Therefore, the radiation beam 6 passes the radiation mask 7 only once on its path between the radiation source 2 and the radiation detector 3.

During scanning, the radiation mask 7 is discretely moved around the object 4 at predetermined angular steps of $\alpha=360°/N$ wherein N is the number of the shielding elements of the ring-shaped radiation mask 7.

Figure 6:
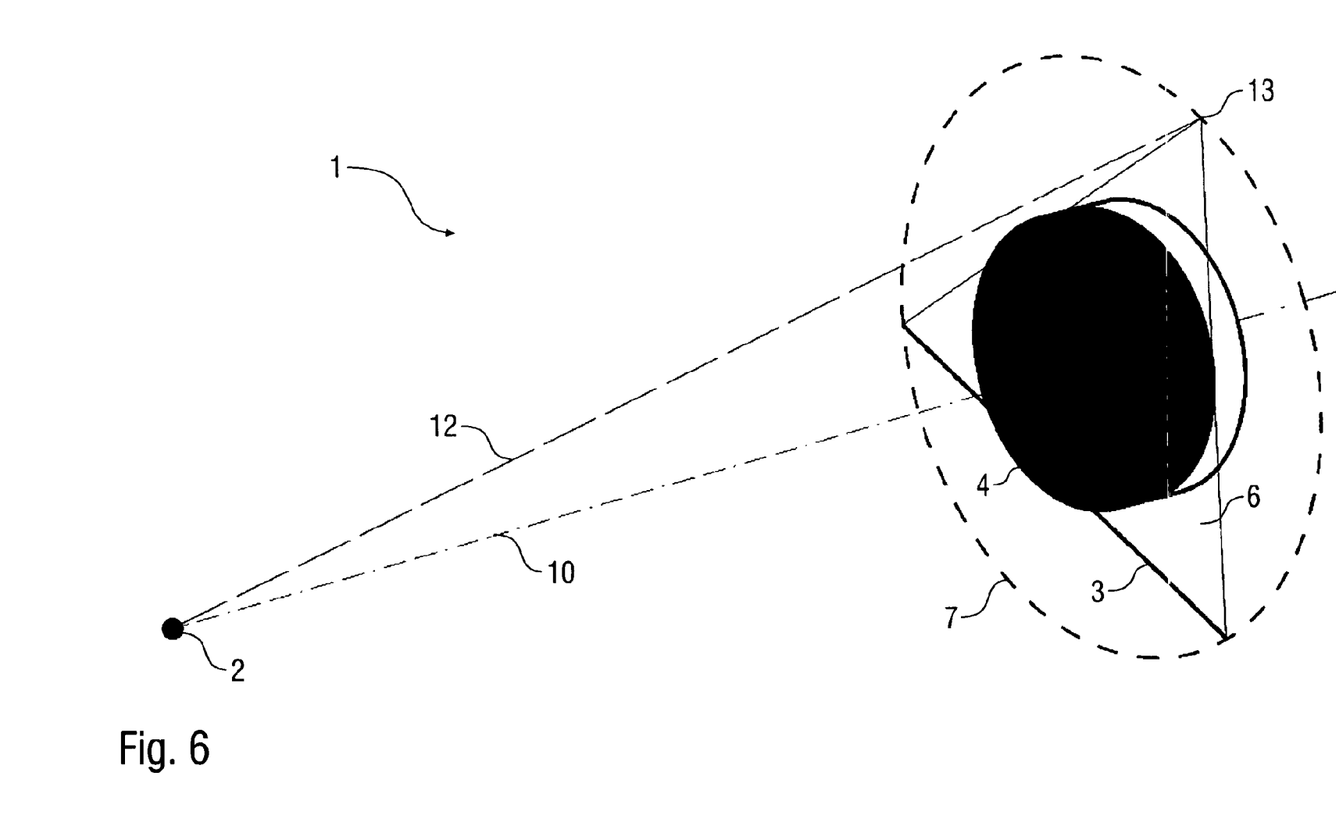
FIG. 6 is a perspective view of a fifth example in which a ring-shaped anode surrounds the object in the measurement plane wherein an electron beam hits the ring-shaped anode and thereby generates a secondary X-radiation beam.

Further, FIG. 6 illustrates the afore-mentioned fifth example which is partially similar to the other examples so that reference is made to the above description and the same reference numerals are used for corresponding parts and details.

The radiation mask 7 consists of a ring-shaped anode which is hit by an electron beam 12 which is generated by the radiation source 2. The target point 13 of the electron beam on the ring-shaped anode generates secondary X-radiation which penetrates the object 4.

The electron beam 12 is moved on the surface shell of a cone surrounding the center axis 10 so that the target point 13 of the electron beam 12 on the ring-shaped anode rotates around the object along the circumference of the ring-shaped radiation mask 7.

Figure 7:
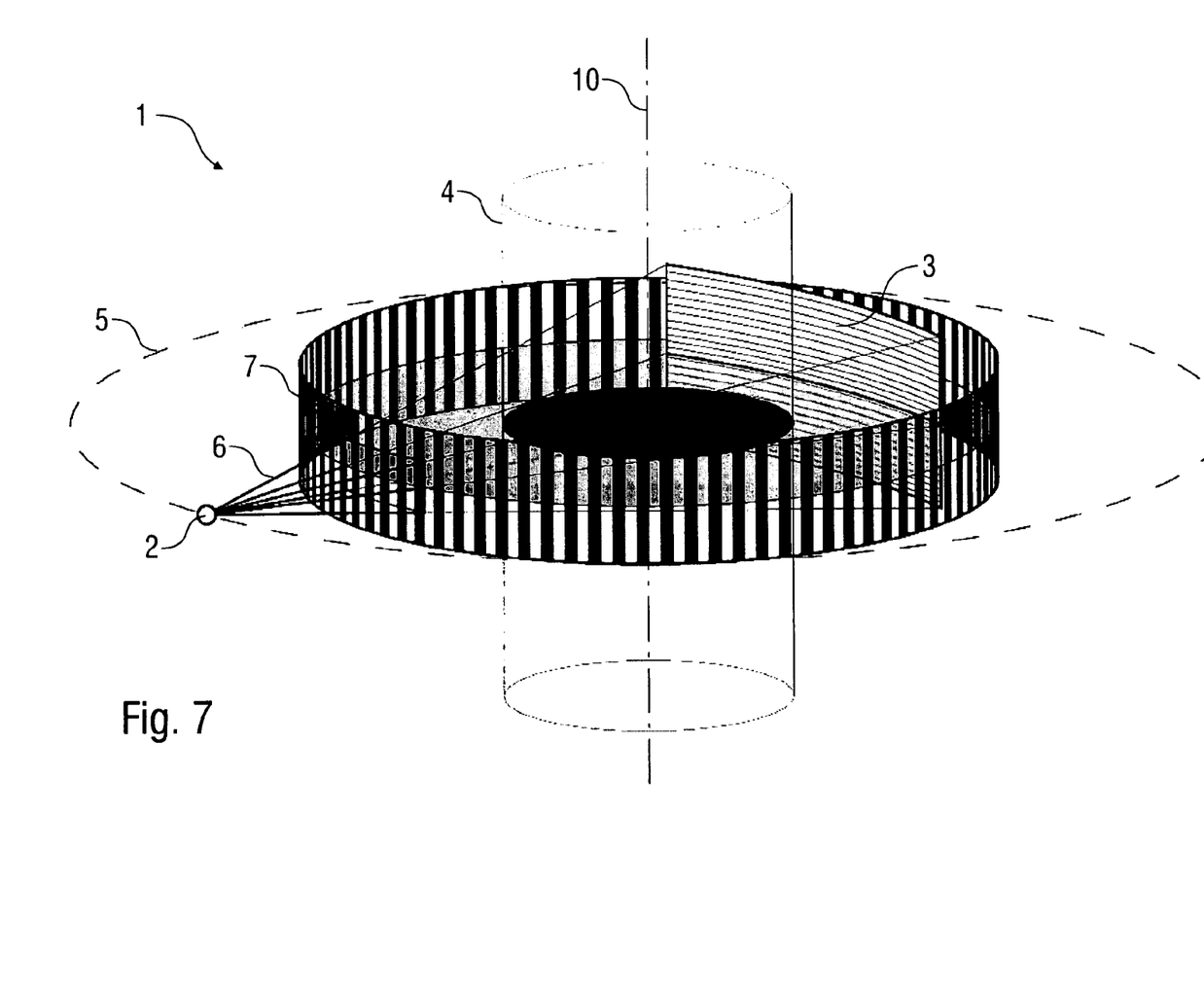
FIG. 7 is a perspective view of a sixth example in which the tomography apparatus generates three-dimensional images of the object.

Finally, FIG. 7 illustrates the sixth example which is partially similar to the other examples so that reference is made to the above description and the same reference numerals are used for corresponding parts and details.

The radiation beam 6 is not restricted to a single measurement plane. Instead, the radiation beam 6 has an axial extension with regard to the central axis 10 which is the rotary axis of the radiation beam 6.

Further, the radiation mask 7 is not restricted to a single measurement plane. Instead, the radiation mask 7 has an axial extension along the central axis 10 so that it masks the entire radiation beam 6 along its axial extension.

Further, the radiation detector 3 has an axial extension along the central axis 10.

Therefore, the tomography apparatus 1 generates three-dimensional images of the object 4 (e.g., a patient) in contrast to the afore-mentioned other examples which merely generate sectional images of the object.

Although our apparatus and methods have been described with reference to the particular arrangement of parts, features and the like, these are not intended to exhaust all possible arrangements of features. Indeed, many other modifications and variations will be ascertainable to those of skill in the art. Further, this disclosure also encompasses the subject matter of the dependent claims without the features of the preceding claims. Therefore, it is possible to cancel any features from the claims without departing from the scope and spirit of our apparatus and methods.

The invention claimed is:

1. A tomography apparatus that generates images of an object, comprising:
   a) a radiation source emitting a radiation beam, wherein the radiation beam rotates around the object and penetrates the object,
   b) a radiation detector rotating around the object opposite the radiation source so that the radiation detector detects the radiation beam after penetration of the object,
   c) a radiation mask surrounding the object that masks the radiation beam,
   wherein the radiation mask is fixed and arranged in a path of the radiation beam between the radiation source and the radiation detector, and the radiation beam passes the radiation mask only once between the radiation source and the rotating radiation detector.

2. The tomography apparatus according to claim 1, wherein
   a) the radiation mask is ring-shaped and surrounds the object, and
   b) the radiation detector is arranged inside the ring-shaped radiation mask.

3. The tomography apparatus according to claim 1, wherein
   a) the radiation source comprises a ring-shaped anode surrounding the object, optionally in the measurement plane,
   b) the radiation source comprises an electron source directing an electron beam onto the ring-shaped anode, thereby generating the radiation beam as a secondary X-radiation beam,
   c) the ring-shaped anode comprises several anode elements spaced apart and distributed around the object so that the anode constitutes or imitates the radiation mask, and
   d) the electron beam is moved around the ring-shaped anode so that the secondary X-radiation beam rotates around the object.

4. The tomography apparatus according to claim 3, further comprising at least one of:
   a) the radiation detector rotates around the object,
   b) the electron beam and the radiation detector are moved in the same direction and with the same angular speed around the object, and
   c) the electron beam is aligned substantially transverse to the measurement plane.

5. The tomography apparatus according to claim 1, further comprising at least one of:
   a) the radiation beam has an axial extension with regard to its rotary axis,
   b) the radiation beam penetrates the object in a three-dimensional area so that the tomography apparatus generates three-dimensional images of the object,
   c) the radiation mask has an axial extension with regard to the rotary axis of the radiation beam so that it masks the radiation beam not only in a single plane, but along the rotary axis of the radiation beam, and d) the radiation detector has an axial extension with regard to the rotary axis of the radiation beam so that it detects the radiation beam not only in a single plane, but along the rotary axis of the radiation beam.

6. The tomography apparatus according to claim 1, further comprising at least one of:
a) the radiation detector is flat or curved,
b) the radiation detector is arranged inside the ring-shaped radiation mask,
c) the radiation beam is fan-shaped and substantially coplanar with the measurement plane,
d) the radiation beam is cone-shaped and penetrates the object through windows of the radiation mask,
e) the radiation detector is radiation-sensitive along a predetermined extension along the measurement plane,
f) the radiation detector is radiation-sensitive along a predetermined extension in two dimensions,
g) the radiation is X-radiation, and
h) the radiation mask is made of a material which is radiation absorbing lead or tungsten.

7. The tomography apparatus according to claim 1, further comprising at least one of:
a) the radiation source and the radiation detector are arranged on a gantry on opposite sides of the object, wherein the gantry rotates in the measurement plane,
b) the radiation beam, the radiation source and the radiation detector carry out coaxial rotary motions,
c) the radiation source rotates around the object,
d) the radiation detector rotates in the same direction and at the same angular speed around the object as the radiation beam,
e) the radiation beam and the radiation detector rotate around the object with the same angular speed and in the same direction so that the radiation source and the radiation detector-are always on opposite sides of the object,
f) rotation of the radiation detector is synchronized with rotation of the radiation beam or the radiation source so that the radiation detector detects the radiation beam after penetration of the object, and
g) the tomography apparatus is a rotate/rotate device comprising a rotating radiation source and a rotation radiation detector.

8. The tomography method that generates sectional images of an object in a measurement plane, comprising:
a) emitting a radiation beam by a radiation source, wherein the radiation beam rotates in the measurement plane relative to the object and penetrates the object,
b) detecting the radiation beam with a radiation detector after penetration of the object, and
c) masking the radiation beam by a radiation mask which surrounds the object, fixed and arranged in a path of the radiation beam between the radiation source and the radiation detector,
wherein the radiation beam passes the radiation mask only once between the radiation source and the rotating radiation detector.

9. The tomography apparatus according to claim 1, wherein the radiation beam passes the radiation mask only once between the radiation source and all radiation detectors.

10. The tomography method according to claim 8, wherein the radiation beam passes the radiation mask only once between the radiation source and all radiation detectors.

* * * * *